(12) United States Patent
Vincent et al.

(10) Patent No.: US 6,932,991 B2
(45) Date of Patent: Aug. 23, 2005

(54) **LEVAN-PRODUCING *LACTOBACILLUS* STRAIN AND METHOD OF PREPARING HUMAN OR PET FOOD PRODUCTS USING THE SAME**

(75) Inventors: Sebastien Vincent, Pully (CH); Markus Brandt, Filderstadt (DE); Christoph Cavadini, Le Mont-Pelerin (CH); Walter P. Hammes, Filderstadt (DE); Jean-Richard Neeser, Savigny (CH); Sabine Waldbuesser, Stuttgart (DE)

(73) Assignee: Nestec S.A., Vevey (CH)

( * ) Notice: Subject to any disclaimer, the term of this patent is extended or adjusted under 35 U.S.C. 154(b) by 239 days.

(21) Appl. No.: 10/465,599

(22) Filed: Jun. 20, 2003

(65) Prior Publication Data

US 2004/0005348 A1 Jan. 8, 2004

Related U.S. Application Data

(63) Continuation of application No. PCT/EP01/14732, filed on Dec. 11, 2001.

(30) Foreign Application Priority Data

Dec. 21, 2000 (EP) ............................................ 00127939

(51) Int. Cl.$^7$ ............................ C12P 19/04; C12N 1/20; C08B 37/00
(52) U.S. Cl. ............................ 426/7; 426/61; 426/658; 127/29; 435/101; 435/252.9
(58) Field of Search .............................. 426/7, 61, 658; 435/101, 252.9; 127/29

(56) References Cited

U.S. PATENT DOCUMENTS

| | | | | |
|---|---|---|---|---|
| 3,891,773 A | * | 6/1975 | Kline et al. ..................... | 426/61 |
| 3,963,835 A | * | 6/1976 | Gryczka ........................ | 426/18 |
| 4,021,581 A | * | 5/1977 | Sing .......................... | 435/252.9 |
| 4,243,687 A | * | 1/1981 | Kline .......................... | 426/62 |
| 4,950,489 A | * | 8/1990 | Spiller ........................ | 426/18 |
| 6,399,119 B1 | * | 6/2002 | Vandamme et al. .......... | 426/18 |
| 6,403,128 B2 | * | 6/2002 | Ueda et al. ................... | 426/18 |
| 6,808,703 B2 | * | 10/2004 | Park et al. .................. | 424/93.4 |

FOREIGN PATENT DOCUMENTS

| | | | |
|---|---|---|---|
| EP | 001283011 A1 | * | 2/2003 |
| JP | 40 1091778 A | * | 4/1989 |
| JP | 2001 242004 A | * | 9/2001 |
| WO | 2004 073418 A1 | * | 9/2004 |

OTHER PUBLICATIONS

Geel–Schutten et al., "Biochemical and Structural Characterization of the Glucan and Frutan Exopolysaccharides Synthesized by the *Lactobacillus reuteri* Wild–Type Strain and by Mutant Strains", Applied and Environmental Microbiology, vol., 65, No. 7, pp. 3008–3014 (1999).

Geel–Schutten et al., "Screening and characterization of Lactobacillus strains producing large amounts of exopolysaccharides", Applied Microbiology and Biotechnology, vol. 65, No. 11, pp. 5003–5008 (1999).

J. Hugenholtz (Abstract) Analysis of sugar metabolism in an EPS productin *Lactococcus lactis* by 31P NMR, Journal of Biotechnology, vol. 77, No. 1, pp. 17–23 (2000).

P. J. Looijesteijn (Abstract) Regulation of exopolysaccharide production by *Lactococcus lactis*, Applied and Environmental Microbiology, vol. 65, No. 11,, pp. 5003–5008 (1999).

F. Stingle,(Abstract,) *Lactobacillus helveticus* lh59 secretes and exopolysaccharide theis is identical to theone produced by *lactobacillus helveticus* Tn–4, a presumed spontaneous mutant of *lactobacillus helveticus* TY 1–2, Carbohydrate Research vol. 302 No. 3–4, pp. 197–202 (1997).

M Staaf,(Abstract)"Structural elucidation of an extracellular polysaccharide produced by *lactobacillus helveticus*", Carbohydrate Research, vol. 302 No. 3–4, pp. 197–202 (1997).

* cited by examiner

*Primary Examiner*—Keith Hendricks
(74) *Attorney, Agent, or Firm*—Winston & Strawn LLP

(57) ABSTRACT

The present invention relates to an isolated and purified strain of the species *Lactobacillus sanfranciscensis* which produces levan. The present invention further relates to a method of producing the levan, and to a method of preparing various human or pet food products or cosmetic products which utilizes the levan and/or a strain producing the same.

20 Claims, 2 Drawing Sheets levan
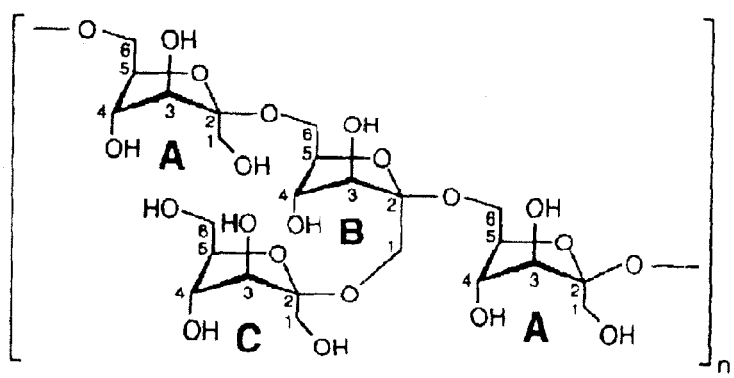
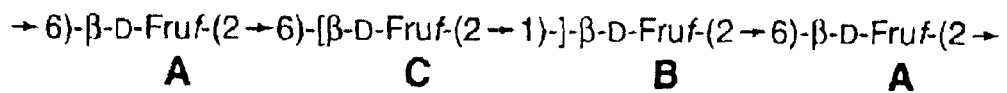
Figure 1 : Structure of the levan produced by *L. sanfransciscensis* CNCM I-2588.

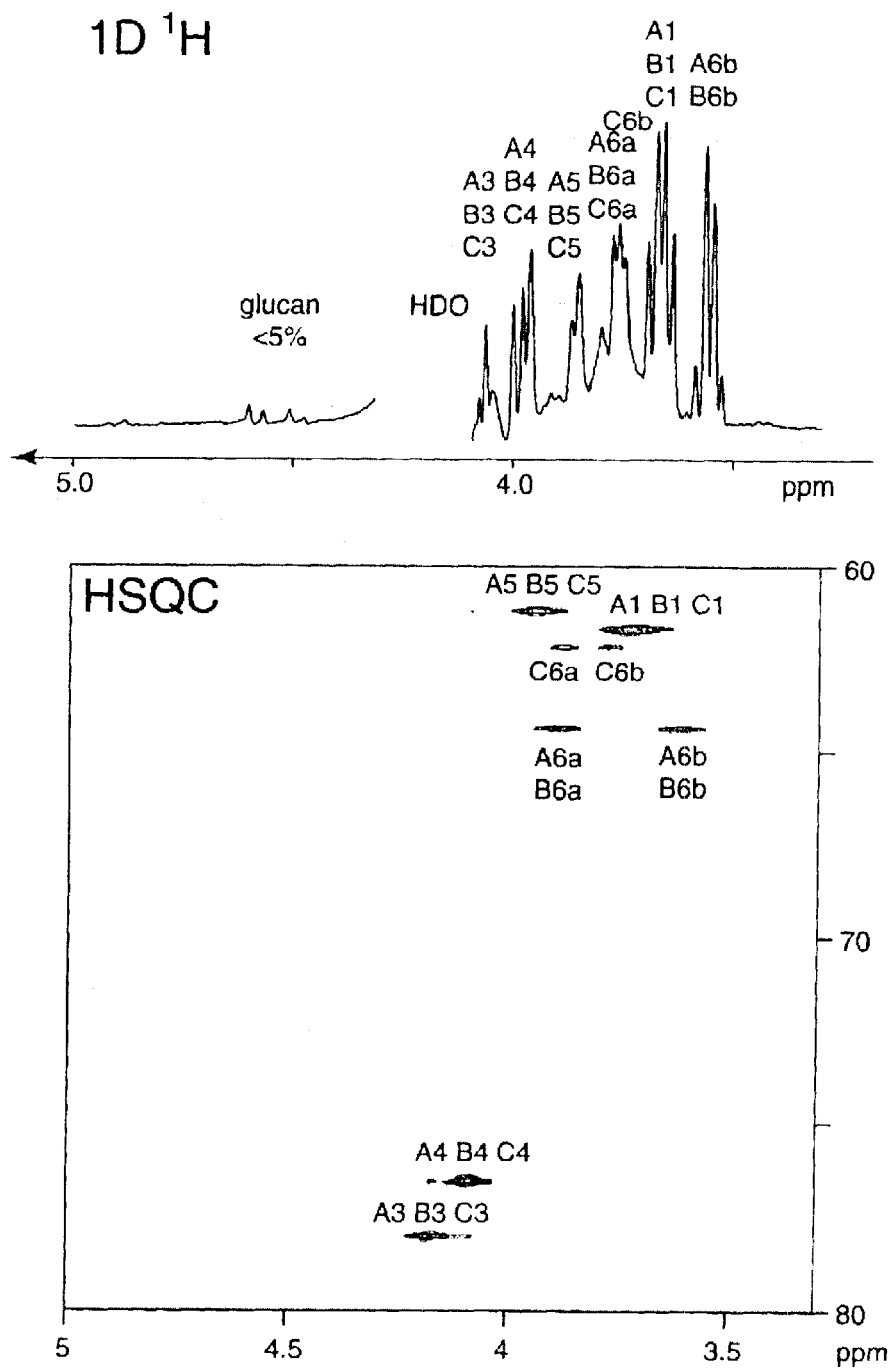
Figure 2 (top) 1D $^1$H NMR spectra of the levan produced by *L. sanfransciscensis* CNCM I-2588 recorded in $^2$H$_2$O at 600 MHz and 67°C. All β D-Fru*f* resonances are identified by the corresponding residue letter code and number; (bottom) PEP-HSQC spectra of the levan produced by *L. sanfransciscensis* CNCM I-2588.

LEVAN-PRODUCING *LACTOBACILLUS* STRAIN AND METHOD OF PREPARING HUMAN OR PET FOOD PRODUCTS USING THE SAME

CROSS-REFERENCE TO RELATED APPLICATIONS

This application is a continuation of International Application PCT/EP01/14732 filed Dec. 11, 2001, the entire content of which is expressly incorporated herein by reference thereto.

FIELD OF THE INVENTION

The present invention relates to a Lactobacillus strain producing as main polysaccharide a levan and its use in various human or pet food products or for the preparation of human or pet food products. The invention also relates to a process for the production of levan.

BACKGROUND OF THE INVENTION

A variety of high-molecular-weight polysaccharides produced by plants (cellulose, pectin and starch), seaweeds (alginate and carrageenan), and bacteria (alginate, gellan, and xanthan) find applications as viscosifying, stabilizing, emulsifying, gelling or water-binding agents in food and non-food industries. All of these polysaccharides are additives, however, and therefore they are considered less desirable in the food industry.

Levans, also known as fructans, β-(2→6)-D-fructoses or β-(2→6)-D-fructans or β-(2→6) -D-fructofuranans or β-(2→6)-D-Fruf or phleins in plants, are natural homopolysaccharides of D-fructofuranose covering a wide range of molecular sizes (~2 kDa to ~60 MDa). Low-molecular-weight levans are produced in plants as carbohydrate reserves (Vandamme, E. J., and Derycke, D. G. (1983) *Adv. Appl. Microbiol.*, 29: 139–176). The molecular structure is in this case a short linear chain of β-(2→6)-fructose. Several types of microorganisms, ranging from plant-associated bacteria, to soil bacteria, dental plaque bacteria, yeasts and fungii, also produce levans (Han, Y. W., (1990) *Adv. Appl. Microbiol.*, 35, 171–194): *Acetobacter, Actinomyces, Aerobacter, Aspergillus, Bacillus, Corynebacterium, Erwinia, Leuconostoc, Pseudomonas, Streptococcus* and others. In microorganisms, levans have higher molecular weights and generally extensive branching through β-(2→1) linkages are present in addition to β-(2→6) linkages seen in plants levans.

Lactic acid bacteria which are food-grade organisms that possess GRAS (generally recognized as safe) status in the USA and are known to produce abundant variety of exopolysaccharide molecules (Cerning, J. (1990) *FEMS Microbiol. Rev.* 87:113–130; Dunican, L. K. and Seeley, H. W. (1965) *J. Gen. Microbiol.* 40: 297–308), which contribute to the texture of fermented milk. Exopolysaccharides from these bacteria may allow development of a new generation of food-grade polysaccharides.

Indeed, synthesis of heteropolysaccharides by lactic acid bacteria, including *Lactobacilli*, is currently being studied intensively (Cerning, J. (1990) *FEMS Microbiol. Rev.* 87: 113–130; Grobben, G. J., et al. (1995) *J. Appl. Bacteriol.* 79: 103107 ; Stingele, F. et al., (1996), *J. Bacteriol.* 178: 1680–1690 and van den Berg, D. J. C., et al., (1995) *Appl. Environ. Microbiol.* 61: 2840–2844).

Also, synthesis of homopolysaccharides (e.g. dextran and levan) has been studied mainly in *Leuconostoc mesenteroides* (NO 6055) and *Streptococci* (Cerning, J. (1990) *FEMS Microbiol. Rev.* 87: 113–130). Limited information is available about homopolysaccharide biosynthesis in *Lactobacilli* (Dunican, L. K. and Seeley, H. W. (1965) *J. Gen. Microbiol.* 40: 297–308; Pidoux, M. et al., (1990) *J. Appl. Bacteriol.* 69: 311–320).

More recently, G. van Geel-Schutten et al. have identified a strain of *Lactobacillus reuteri* LB 121 which synthesizes water-soluble exopolysaccharide material with both glucose and fructose and further characterized these glucan and fructan exopolysaccharides (van Geel-Schutten, G. H., et al., (1999), *Appl. Environ. Microbiol.* 65: 3008–3014).

Thus, it would be of interest to provide other strains of *Lactobacilli*, and especially outside of the *Lactobacillus reuteri* species, that are able to produce fructans, and especially levan, and that would present a great interest for food industries.

SUMMARY OF THE INVENTION

Accordingly, in a first aspect the present invention aims to provide an isolated and purified *Lactobacilli* strain, more particularly from the species *Lactobacillus sanfranciscensis*, which produces as a levan as a main polysaccharide.

It has been surprisingly found that *Lactobacillus sanfranciscensis* originally used in traditional dough fermentation, can produce levan and a minimal amount of glucose polymer.

The present invention further relates to a method of producing levan from *Lactobacillus sanfranciscensis* strain, which comprises the steps of: inoculating a culture medium containing sucrose with a preculture of said strain; allowing the culture medium to ferment at 25–35° C. for 12 to 48 h; decreasing the pH of the resulting culture to lower than 4.5; and, adding cold ethanol to the culture and storing it at 0 to 10° C. for 6 to 48 h.

The present invention further relates to a method of preparing various human or pet food products or cosmetic compositions which comprises using such polysaccharide and/or a strain that produces the same.

In still another embodiment, the invention relates to a human or pet food product or cosmetic composition comprising at least the highly soluble levan as described above and/or the *Lactobacillus sanfranciscensis* strain as described above.

BRIEF DESCRIPTION OF THE DRAWING FIGURES

FIG. 1: Structure of the levan produced by *L. sanfransciscensis* CNCM I-2588 with monosaccharide units identified by their residue letter code (A to C).

FIG. 2: (top) 1D $^1$H NMR spectra of the levan produced by *L. sanfransciscensis* CNCM I-2588 recorded in $^2$H$_2$O at 600 MHz and 67° C. All b-(-D-Fruf resonances are identified by the corresponding residue letter code and number; (bottom) PEP-HSQC spectra of the levan produced by *L. sanfransciscensis* CNCM I-2588.

DETAILED DESCRIPTION OF THE PREFERRED EMBODIMENTS

Within the following description, the following abbreviations have been used: GRAS, generally recognized as safe; HMBC, heteronuclear multiple-bond correlation; PEP-HSQC, preservation of equivalent pathways in heteronuclear single-quantum coherence; NMR, nuclear magnetic resonance; NOESY, nuclear Overhauser effect spectroscopy;

RAPD PCR, Random Amplified Polymorphic DNA polymerase chain reaction; TOCSY, total correlation spectroscopy; TPPI, time proportional phase increments. Finally, "NCC" designates Nestlé Culture Collection (Nestlé Research Center, Vers-chez-les-Blanc, Lausanne, Switzerland).

According to a first aspect, the present invention relates to an isolated and purified strain of the species *Lactobacillus sanfranciscensis*, which produces levan.

Indeed, it has been surprisingly found that *Lactobacillus sanfranciscensis* originally used in traditional dough fermentation, can produce a highly soluble fructose-containing carbohydrate, especially levan and a minimal amount of glucose polymer.

Preferably, the *Lactobacillus sanfranciscensis* strain is *L. sanfranciscensis* NCC 2729, having the deposit number CNCM I-2588 or *L. sanfranciscensis* NCC 2731, having the deposit number CNCM I-2589 or *L. sanfranciscensis* NCC 2733, for example.

Although levans are more soluble than inulin, their solubility at low temperature is variable and tends to be low (Han, Y. W., (1990) *Adv. Appl. Microbiol.*, 35, 171–194). In contrast, the levan produced by *Lactobacillus sanfranciscensis* is highly soluble even at low temperature.

The levan produced by fermentation of *Lactobacillus sanfranciscensis* NCC 2729 was analysed by NMR. The major (>95%) product is a levan and the secondary product (<5%) is likely to be a glucan. Enzymic digestion with a specific levanase from *Actinomyces viscosus* showed that the levan produced by said strain has $\beta$-(2→6) linkages. The increased degradation by enzymic digestion with inulinase de *A. niger* suggests that also $\beta$-(2→1) linkages might be present.

In a most preferred embodiment, the *Lactobacillus sanfranciscensis* strains NCC 2729 and NCC 2731 have been deposited by way of example at the Institut Pasteur, 28 rue du Docteur Roux, F-75024 Paris cédex 15, FRANCE, on Dec. 1$^{st}$, 2000, under the deposit numbers CNCM I-2588 and CNCM I-2589, respectively. Details of these strains, concerning especially their morphology, the fermentation of sugars and other aspects, are given below.

Defined Medium

In order to grow colonies of *Lactobacillus sanfranciscensis*, the following medium was used:

| ingredient | quantities | preferably |
|---|---|---|
| sucrose | 0.2–50 g/l | 20 g/l |
| trypton | 0.2–20 g/l | 10 g/l |
| yeast extract | 0.2–20 g/l | 7 g/l |
| diammonium citrate | 0.1–20 g/l | 5 g/l |
| sodium acetate (× 3 in water) | 0.1–20 g/l | 5 g/l |
| KH$_2$PO$_4$ × 3 H$_2$O (× 3 in water) | 0.1-20 g/l | 2.5 g/l |
| beef extract (Lab Lemco powder) | 0.1–20 g/l | 2 g/l |
| potassium gluconate | 0.1–20 g/l | 2 g/l |
| cystein-HCl | 0.01–10 g/l | 0.5 g/l |
| MgSO$_4$ (× 7 in water) | 0.01–10 g/l | 0.2 g/l |
| MnSO$_4$ (× 4 in water) | 0.01–10 g/l | 0.1 g/l |
| FeSO$_4$ (× 7 in water) | 0.001–2 g/l | 0.05 g/l |
| Tween 80 | 0.1–10 ml | 1 ml |

Finally, the pH was corrected to a value between 5 and 6, preferably 5.4, with addition of 3N KOH.

Morphology

The *Lactobacillus sanfranciscensis* are Gram positive microorganisms shaped as straight rods. They form regular white colonies on the defined medium agar plates.

Upon addition of >2% sucrose the colonies become extended in size and attend slimy appearance.

*L. sanfranciscensis* are catalase-negative and facultative anaerobes.

Fermentation of Sugars

For the fermentation of sugars, *L. sanfranciscensis* are mandatory heterofermentative. They produce D/L-lactic acid (D/L=40/60) from maltose. *L. sanfranciscensis* have a proteolytic activity on wheat proteins and are capable of fermenting several complex carbohydrates including maltose, glucose and sucrose.

Other Aspects

The *L. sanfranciscensis* strains described synthesize levan polysaccharide. The strains can be identified by RAPD PCR, a method for creating genomic fingerprints from species of which little is known about target sequence to be amplified by amplifying strain-specific arrays of DNA fragments (fingerprints) by PCR amplification using arbitrary oligonucleotides to prime DNA synthesis from genomic sites which they fortuitously match or almost match. DNA amplified is this manner can be used to determine the relatedness of species by matching characteristic patterns.

According to a further aspect, the present invention relates to a method of producing levan which comprising: inoculating a medium containing sucrose with a preculture of a strain of *L. sanfranciscensis* according to the invention, allowing the medium to subsequently ferment at 25–35° C. for 12 to 48 h, preferably 24 h, feeding sucrose. The culture medium preferably contains at least 0.2% sucrose.

After a decrease of the pH value to lower than 4.5, the culture is harvested. To obtain the levan, 2 volumes of ice cold ethanol is added to the supernatant. After being stored at 0 to 10° C., preferably 4° C., for 6 to 48 h, preferably 15 h, the levan in the sediment can be further purified by dissolving in distillated water and subsequent precipitation by ethanol.

For growing the *L. sanfranciscensis* bacteria and obtaining levan, growth may be carried out in the specially defined medium described earlier (20 g/l sucrose, trypton 10 g/l, yeast extract 7 g/l, diammonium citrate 5 g/l, sodium acetate (×3 in water) 5 g/l, KH$_2$PO$_4$×3 H2O (×3 in water) 2.5 g/l, beef extract (Lab Lemco powder) 2 g/l, potassium gluconate 2 g/l, cystein-HCl 0.5 g/l, MgSO$_4$ (×7 in water) 0.2 g/l, MnSO$_4$ (×4 in water) 0.1 g/l, FeSO$_4$ (×7 in water) 0.05 g/l, tween 80 1 ml, and pH corrected to 5.4 using 3N KOH).

*Lactobacillus sanfranciscensis* cultures supernantants containing levan can be dried to give a levan powder, for example. Preferably, the culture is dried by lyophilisation, spray drying, freeze-drying, fluidised bed drying, for example.

The production of a highly soluble levan by GRAS *Lactobacillus sanfranciscensis* bacteria strain allows its application in various fields. According to a further aspect, the invention relates to a method of preparing various human or pet food products or cosmetic compositions which comprises utilizing such polysaccharide and/or said *Lactobacillus sanfranciscensis*. Preferably, the polysaccharide according to the invention may be used for the preparation of infant formula, milk-based products, cereal-based products, salad dressings, sauces, ketchup, mustard, for example.

The polysaccharide according to the present invention can also be used for the preparation of fermented cereals, milk, fruits or vegetables juices such as fermented "self-textured" tomato juice (that can be further used for ketchup with dietary fibres and improved texture), milk drinks supplemented with extracellular polysaccharide, fermented foods and vegetables (papes/compotes, juices, food preparations for ice-cream, etc.), as a polysaccharide-containing powder obtained by spray-drying, that finds applications as a thickener in dehydrated products (such as soups and sauces).

In another embodiment, the levan from *Lactobacillus sanfranciscensis* may be used as a source of prebiotic fructans in human or pet food products. The main biological property of fructo-oligo- and poly-saccharides (FOS) is their ability to selectively foster the growth of bifidobacteria once reaching the human (or mammalian) large intestine. To date, only β-(2→1)-D-fructose oligo- and polymers such as inulin have been described as being bifidogenic and are consequently classified as prebiotic carbohydrates. In order to ferment such fructans, the bifidobacteria from the normal microflora have to use specific enzymes, namely fructosidases. Such microbial enzymes could also be able to hydrolyse β-(2→6)-fructoses offering a nutritional advantage to levans as being prebiotic polysaccharides. It has been recently shown that *Bifidobacteria* can hydrolyse β-(2→6)-fructoses (Marx et al. (2000), *FEMS Microbiol. Letters* 182,163–169).

Levan may also be used as a source of immunologically-stimulating polysaccharide (P. Z. Allen and W. H. Bowen, (1990) *Arch. Oral. Biol.*, 35, 55–62).

Accordingly, the levan according to the present invention may be present in the human or pet food product in an amount of from about 0.01% to about 25%, and more preferably from 0.1% to 20%. In applications in the field of cosmetics, the levan according to the present invention may be present in an amount of from about 0.01% to about 5%, and more preferably from 0.1% to 2%.

The strain according to the invention may be used in the human or pet food product, as well as in cosmetics, in an amount of at least $1 \times 10^5$ cfu/g and more preferably $10^7$ cfu/g to $>10^8$ cfu/g.

Finally, the present invention relates to a human or pet food product or composition comprising at least the polysaccharide as described above, the bacterial strain as described above, or the levan produced by the bacterial strain described above.

To prepare such a food product or composition, levan obtained as described above can be incorporated into a food or cosmetic product, such as cereal powder, milk powder, a yogurt, a ketchup, a mayonnaise or a skin cream, during its manufacture, for example.

A pet food product may comprise as a source of prebiotic the levan from *L. sanfranciscensis* and/or the *L. sanfranciscensis* strain. It may then be a nutritionally complete pet food or a supplement or a treat or a biscuit. It is preferred to include the levan and/or the strain in a nutritionally complete pet food.

The nutritionally complete pet food may be in any suitable form; for example in dried form, semi-moist form and wet form. These pet foods may be produced as is conventional. Apart from the nutritional agent, these pet foods may include any one or more of a starch source, a protein source and lipid source. Suitable starch sources are, for example, grains and legumes such as corn, rice, wheat, barley, oats, soy, and mixtures of these. Suitable protein sources may be selected from any suitable animal or vegetable protein source; for example meat and meal, poultry meal, fish meal, soy protein concentrates, milk proteins, gluten, and the like. Suitable lipid sources include meats, animal fats and vegetable fats. The choice of the starch, protein and lipid sources will be largely determined by the nutritional needs of the animal, palatability considerations, and the type of product produced. Further, various other ingredients, for example, sugar, salt, spices, seasonings, vitamins, minerals, flavoring agents, fats and the like may also be incorporated into dried food as desired.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing.

A suitable process is described in European patent application No 0850569; the disclosure of which is incorporated herein by reference thereto. If the bacterial strain is used, the organism is best coated onto or filled into the dried pet food. A suitable process is described in European patent application No 0862863; the disclosure of which is incorporated herein by reference thereto.

For wet foods, the processes described in U.S. Pat. Nos. 4,781,939 and 5,132,137 may be used to produce simulated meat products. The disclosures of these patents are also incorporated herein by reference thereto. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

The maximum level of levan as prebiotic in the pet food is preferably about 20% by weight; especially about 10% by weight. For example, the prebiotic may comprise about 0.1% to about 20% by weight of the pet food.

EXAMPLES

The following examples are given by way of illustration only and in no way should be construed as limiting the subject matter of the present application. All percentages are given by weight unless otherwise indicated. The examples are preceded by a brief description of the figures.

Example 1

Testing for the Strains of *Lactobacillus Sanfranciscensis* which Produce Levan

Strains were grown on defined medium-agar plates as described earlier: 20 g/l sucrose, trypton 10 g/l, yeast extract 7 g/l, diammonium citrate 5 g/l, sodium acetate (×3 in water) 5 g/l, $KH_2PO_4 \times 3$ $H_2O$ (×3 in water) 2.5 g/l, beef extract (Lab Lemco powder) 2 g/l, potassium gluconate 2 g/l, cystein-HCl 0.5 g/l, $MgSO_4$ (×7 in water) 0.2 g/l, $MnSO_4$ (×4 in water) 0.1 g/l, $FeSO_4$ (×7 in water) 0.05 g/l, tween 80 1 ml, and pH corrected to 5.4 using 3N KOH).

Strains reaching a slimy appearance were subsequently grown in liquid special medium, then allowed to ferment at 25–35° C. for 12 to 48 h, preferably 24 h. After a drop of the pH to a value smaller than 4.5, the culture was harvested. To obtain the levan, 2 volumes of ice cold ethanol were added to the supernatant, and after storage at 0 to 10° C., preferably 4° C., for 6 to 48 h, preferably 15 h, the levan in the sediment was further purified by dissolving the sediment in distillated water and precipitation of the levan by ethanol.

The *Lactobacillus sanfranciscensis* are shaped as straight rods and they form regular white colonies on the defined medium agar plates.

Upon addition of >2% sucrose, the colonies become extended in size and attend slimy appearance, which allows a macroscopic identification.

For the fermentation of sugars, *L. sanfranciscensis* are mandatory heterofermentative. They produce D/L-lactic acid (D/L=40/60) from maltose. *L. sanfranciscensis* have a proteolytic activity on wheat proteins and are capable of fermenting several complex carbohydrates including maltose, glucose and sucrose.

The *L. sanfranciscensis* strains CNCM I-2588 and CNCM I-2589 described synthesize levan polysaccharide. The strains can be identified by RAPD PCR, a method for creating genomic fingerprints from species of which little is known about target sequence to be amplified by amplifying strain-specific arrays of DNA fragments (fingerprints) by PCR amplification using arbitrary oligonucleotides to prime DNA synthesis from genomic sites which they fortuitously match or almost match. DNA amplified is this manner can be used to determine the relatedness of species by matching characteristic patterns.

Example 2

Structural Analysis of the Polysaccharide produced by *Lactobacillus sanfransciscensis* CNCM I-2588

The characterisation was carried out by monosaccharide analysis, nuclear magnetic resonance spectroscopy (NMR) and enzymatic digestion.

Monosaccharide Analysis

Quantitative monosaccharide analysis of the polysaccharide produced by *L. sanfranciscensis* CNCM I-2588 was performed by high-performance anion-exchange (HPAE) chromatography with pulsed amperometric detection (PAD) after soft acid hydrolysis (2 N trifluoroacetic acid, 60° C., samples taken at 30 minutes and 1 h). Low temperature hydrolysis conditions were necessary for avoiding degrading fructose monosaccharide units (into mannose and glucose).

The analysis showed the presence of >95% of fructose and traces of glucose.

NMR Spectroscopy 5 mg of polysaccharide produced by *L. sanfranciscensis* CNCM I-2588 were dissolved in 99.96 atom % $^2H_2O$ (Euriso-Top). All experiments were recorded on a three-channel Bruker DRX 600 MHz spectrometer equipped with an actively shielded pulsed-field z-gradient inverse triple-resonance probe. Chemical shifts are given in ppm by reference to the α-anomeric signal of external $[^{13}C-1]$-glucose ($\delta_{H-1}$ 5.15 for H-1 and $\delta^{C-1}$ 92.90 for C-1).

Phase-sensitive two-dimensional experiments were recorded using TPPI (Marion, D. et al., (1983) *Biochem. Biophys. Res. Commun.* 113, 967–974): TOCSY (Braunschweiler, L. et al., (1983) *J. Magn. Reson.* 53, 521–528) with mixing times between 15 ms and 90 ms, NOESY (Jeener, J. et al., (1979) *J. Chem. Phys.* 11, 4546–4553; Anil Kumar, Ernst, R. R. et al. (1980) *Biochem. Biophys. Res. Commun.* 95, 1–6) with mixing times between 50 ms and 200 ms and a gradient sensitivity-enhanced $^1H$-$^{13}C$ heteronuclear single-quantum coherence (PEP-HSQC) (Kay, L. E., et al. (1992) *J. Am. Chem. Soc.* 114, 10663–10665). A magnitude mode gradient-filtered 50 ms $^1H$-$^{13}C$ HMBC (Bax, A. et al. (1986) *J. Am. Chem. Soc.* 108, 2093–2094) was recorded for determining glycosidic linkages.

The following number of complex points were acquired ($F_1$, $F_2$): 256×1024 (TOCSY and NOESY), 512×1024 (HSQC) and 256×4096 (HMBC), with averaging over 16 scans (TOCSY, HSQC) or 64 scans (NOESY, HMBC). Spectral widths (($\omega_1$, $\omega_2$) of either 1800 Hz×1800 Hz (TOCSY and NOESY) or 3020 Hz×1800 Hz (HSQC and HMBC) were used. A 90° shifted square sine-bell was used in all cases, with zero-filling once. All data were processed using Bruker XWINNMR 2.6 software.

The 1D $^1H$ NMR spectra of the polysaccharide produced by *L. sanfranciscensis* CNCM I-2588 (FIG. 2) showed one dominant set of proton resonances labeled A. Additional sets of resonances of much lower amplitudes (integrals<5% than A) around 5 ppm were attributed to anomeric resonances of glucans and were not assigned further.

After analysis of the two-dimensional spectra, the $^1H$ and $^{13}C$ NMR assignments were obtained and are collected in Table I.

TABLE I $^1H$ and $^{13}C$ NMR chemical shifts of the polysaccharide produced by *L. sanfranciscensis* CNCM I-2588 determined in $^2H_2O$ at 67° C.

| | H-1a C-1 | H-1b | C-2 | H-3 C-3 | H-4 C-4 | H-5 C-5 | H-6a C-6 | H-6b |
|---|---|---|---|---|---|---|---|---|
| A →6β-D-Fruf-(2→ | 3.73 61.7 | 3.70 | 105.2 | 4.17 78.0 | 4.08 76.6 | 3.94 81.2 | 3.88 64.4 | 3.62 |
| B →1,6)-β-D-Fruf-(2→ | 3.73 61.7 | 3.70 | 105.2 | 4.18 78.3 | 4.07 76.4 | 3.94 81.2 | 3.90 64.3 | 3.63 |
| C β-D-Fruf-(2→ | 3.73 61.7 | 3.70 | 105.2 | 4.18 78.3 | 4.08 76.4 | 3.94 81.2 | 3.87 62.2 | 3.77 |

The values are given in ppm relative to external $[^{13}C-1]$glucose ($\delta_{H-1(\alpha)}$ 5.15 and $\delta_{C-1\,(\alpha)}$ 92.90).

The $^1H$ assignment of the polysaccharide produced by *L. sanfranciscensis* CNCM I-2588 was achieved by following all traces in the TOCSY and NOESY spectra recorded. The $^{13}C$ resonances were obtained from the PEP-HSQC spectrum at the exception of the C-2 resonance, C-2 being a quaternary carbon it was not expected to yield a signal in a PEP-HSQC, which was obtained from the HMBC spectrum via its long-range scalar coupling to both H-1 and H-3.

Assignment of the most abundant residue A corresponds to the chemical shifts of a β-D-Fruf monosaccharide unit (van Geel-Schutten, G. H. et al., (1999), *Appl. Environ. Microbiol.* 65: 3008–3014). The less abundant residues B and C, corresponding to smaller intensity NMR peaks, also correspond to β-D-Fruf monosaccharide units (Table 1, J. W. Timmermans et al., (1993), *Carbohydr. Res.* 243: 379–384) of differing substitution. Integrals of PEP-HSQC peaks give quite a precise idea of the ratio of the different species. From (C-6, H-6) methylene cross-peaks, A+B: C is 5.5 : 2, while from (C-1, H-1) methylene cross-peaks, A+B+C=6.7. On the other hand, (C-i, H-i) cross-peaks with i=3,4,5 indicate that A+B+C=4.1. From these values, it can be concluded that the repeating unit has two non-branched Fruf, one branching point Fruf and one terminal Fruf. The structure is shown in FIG. 1.

The substitution pattern is nevertheless difficult to ascertain, since neither proton nor carbon chemical shifts are substancially modified following glycosidic substitution at positions 1 or 2 (J. W. Timmermans et al., (1993), *Carbohydr. Res.* 243: 379–384). In case of substitution at the 6 position, the carbon chemical shift are above 64 ppm while for unsubstituted C-6, they are around 63 ppm. NOESY and HMBC data were of little help, as is common in homopolysaccharides, since intraresidue transfers overlap with possible interresidue transfers. In the absence of methylation analysis data, the substitution can be inferred to be on positions 1, 2, and 6.

Enzymatic Digestions

Enzymatic digestion with a specific levanase from *Actinomyces viscosus* showed that the levan produced by said strain has β-(2→6) linkages. The increased degradation by enzymatic digestion with inulinase de *Aspergillus niger* suggests that also β-(2→1) linkages might be present.

In conclusion, based on chemical monosaccharide analysis and NMR spectroscopy, the structure of the repeating unit of the polysaccharide secreted by *L. sanfranciscensis* CNCM I-2588 can be formulated as →6)-β-D-Fruf-(2→6)-[β-D-Fruf-(2→1)-]-β-D-Fruf-(2→6)-β-D-Fruf-(2→ and is represented in FIG. 1.

Example 3

Preparation of the Levan According to the Invention

After growth on the defined medium (20 g/l sucrose, trypton 10 g/l, yeast extract 7 g/l, diammonium citrate 5 g/l, sodium acetate (×3 in water) 5 g/l, $KH_2PO_4$×3 H2O (×3 in water) 2.5 g/l, beef extract (Lab Lemco powder) 2 g/l, potassium gluconate 2 g/l, cystein-HCl 0.5 g/l, $MgSO_4$ (×7 in water) 0.2 g/l, $MnSO_4$ (×4 in water) 0.1 g/l, $FeSO_4$ (×7 in water) 0.05 g/l, tween 80 1 ml, and pH corrected to 5.4 using 3N KOH) at 25–35° C. for 24 h, the culture supernatant was harvested (after sucrose consumption) and centrifuged (10 min, 1000 g, 4° C.) to remove cells.

Then, 1 volume of ice cold ethanol were added. After stirring and cooling at 4° C., for 15 h, precipitated extracellular polysaccharide was recovered by centrifugation (30 min, 15000 g, 4° C.).

Precipitate was dissolved in distilled water, harvested again and to the supernatant 1 volume Ethanol was added (storage at 4° C., for 15 h). After centrifugation (27000×g, 25 min) the precipitate was dissolved in distilled water and and dialysed against demineralized water for two days (molecular weight cut-off 12000–14000 Da) and lyophylized.

Example 4

Use of *L. Sanfranciscensis* Strain in Dairy Products

The strain *L. sanfranciscensis* CNCM I-2588 or CNCM I-2589 according to the present invention is used for the manufacture of fermented yogurt-like milk products.

To do this, 1l of a milk product containing 2.8% of fats and supplemented with 2% of skimmed milk powder and 6% of sucrose is prepared, it is pasteurized at 96° C. for 30 minutes and its temperature is then lowered to 42° C. Precultures of a non-thickening strain of *Streptococcus thermophilus* and of a non-viscous strain *Lactobacillus bulgaricus* are reactivated in a sterile MSK culture medium containing 10% of reconstituted milk powder and 0.1% of commercial yeast extract.

A preculture of the strain of *L. sanfranciscensis* is also reactivated in the defined medium defined earlier and then in a sterile MSK culture medium containing 10% of reconstituted milk powder and 0.1% of commercial yeast extract with 1% sucrose. The pasteurized milk product is then inoculated with 1% of each of these reactivated precultures and this milk product is then allowed to ferment at 32° C. until the pH reaches a value of 4.5.

Fermented milks yogurt-like products are produced in this way and stored at 4° C. These Fermented milks yogurt-like products, prepared with a strain of *L. sanfranciscensis*, have an unctuous texture with a pleasant taste, especially after storage for 10 days at 4° C. Moreover, the levan has a prebiotic potential.

Example 5

Use of Levan from *L. sanfranciscensis* Strain as Prebiotic in Infant Formula

A dry mix to be used in dry infant formulas was prepared, for 100 g of formula: 5 to 20%, preferably 10% of peptides, 2 to 40%, preferably 20% of fat, 10 to 60%, preferably 40% of non-levan carbohydrates (including lactose 65%, maltodextrin 20%, starch 15%), and 1 to 10%, preferably 3% of levan (prepared according to example 3), traces of vitamins and oligoelements to meet daily requirements, and 0.1 to 5%, preferably 1.5%, of minerals.

Example 6

Infant Formula Containing Levan from *L. sanfranciscensis*.

To obtain an infant formula we prepared the following mixture containing for 100 ml of formula: 0.5 to 5%, preferably 2% of peptides, 0.2 to 10%, preferably 4% of fat, 1 to 25%, preferably 8% of non-levan carbohydrates (including lactose 65%, maltodextrin 20%, starch 15%), and 0.5 to 20%, preferably 5% of levan (prepared according to example 3), traces of vitamins and oligoelements to meet daily requirements, and 0.01 to 2%, preferably 0.3%, of minerals, and 50 to 90%, preferably 75% of water.

Example 7

Fermented Cereal Based Beverage

The following ingredients were mixed in a container suitable for heat treatment (parts expressed in kilograms): 19.8 rice flour, 15.0 wheat flour, 13.9 oats flakes, 24.3 sucrose, 1.5 yeast extract and 850 water.

The above mixture was then injected with steam up to get a temperature of 130° C. and further kept at that temperature for 1 min., and finally cooled at approx. 32° C. The resulting slurry was then transferred into a fermentation tank, then inoculated with one strain of *L. sanfranciscensis* strain CNCM I-2588 or CNCM I-2589 to obtain a cell concentration in the slurry of about $1–5×10^6$ cfu/ml.

The fermentation took place at 32° C. for 8 hours resulting in an acidified fermented cereal base. The fermented cereal base can be stored for up to 1 week at 4° C. before using or pasteurized/sterilized for long term storage.

Example 8

Pet Food Containing *L. sanfranciscensis* Strain

A feed mixture is made up corn, corn gluten, chicken and fish, salts, vitamins and minerals. The moistened feed leaving the preconditioner is then fed into an extruder-cooker and gelatinised. The gelatinised matrix leaving the extruder is forced through a die and extruded. The extrudate leaving the die head is cut into pieces suitable for feeding to dogs, dried at about 110° C. for about 20 minutes, and cooled to form pellets. The resulting water activity of the pellets is about 0.6.

The pellets are sprayed with a coating substrate comprising tallow fat. In addition to the standard coating a dried and concentrated powder containing levan (prepared according to example 3) produced by *L. sanfranciscensis* strain CNCM I-2588 or CNCM I-2589 is coated on the pellets at a rate of 0.1 to 20%, preferably 0.5 to 5%.

Accordingly, the dry dog food obtained thereof is particularly intended for providing a pet a prebiotic source of levan, which improves the composition of the gut microflora or skin and coat conditions, for example.

Example 9

Wet Pet Food Product Containing Levan from *L. sanfranciscensis*.

A mixture is prepared from 73% of poultry parts, pig lungs and beef liver (ground), 16% of wheat flour, 7% of water, 2% of dyes, flavours, vitamins, and inorganic salts. This mixture is emulsified at 12° C. and extruded in the form of a pudding which is then cooked at a temperature of 90° C. It is cooled to 30° C. and cut in chunks. 45% of the chunks are mixed with 55% of a sauce prepared from 98% of water, 1% of dye and 1% of the polysaccharide levan produced by L. sanfranciscensis CNCM I-2588 or CNCM I-2589 and prepared according to example 3 as a thickener with prebiotic properties. Tinplate cans are filled and sterilized at 125° C. for 40 min.

Example 10

Fermented Cereal-based Infant Formula

Wheat, rice or maize flower or a mixture thereof and water having a dry matter content between 20 to 60%, preferable 30 to 50%, and even more preferable between 35 to 45% is inoculated with one strain of L. sanfranciscensis strain CNCM I-2588 or CNCM I-2589 to obtain a cell concentration in the slurry of about $1-5\times10^6$ cfu/ml . Fermentation is carried out at 32° C. for 10 hours. During growth of the strain(s) levan is produced in situ. The fermented and acidified flower is subsequently sterilized by steam injection (120–140° C.) and dried by roller-drying (120–140° C.) or by extrusion cooking (140–180° C.) resulting in an infant formula enriched with the prebiotic exopolysaccharide levan.

What is claimed is:

1. An isolated and purified strain of the species *Lactobacillus sanfranciscensis*, which produces levan.

2. The strain according to claim 1, having the deposit number CNCM I-2588 or CNCM I-2589.

3. A soluble levan produced by the strain according to claim 1.

4. A method of producing levan, which comprises:
   inoculating a culture medium which includes sucrose with a preculture of a strain according to claim 1;
   allowing the culture medium to ferment at 25–35° C. for 12 to 48 h;
   lowering the pH of the resulting culture to below 4.5, and;
   adding cold ethanol to the culture medium and storing it at 0 to 10° C. for 6 to 48 h.

5. The method according to claim 4 wherein the culture medium contains at least 0.2% sucrose.

6. The method according to claim 4, which further comprises purifying the levan in the sediment after storing the culture medium.

7. The method according to claim 4, which further comprises drying the culture medium to produce a levan powder after storing the culture medium.

8. A method of preparing a human or pet food product or a cosmetic composition which comprises adding the levan according to claim 3 to said human or pet food product or cosmetic composition.

9. A method of preparing a human or pet food product or a cosmetic composition which comprises adding the *Lactobacillus sanfranciscensis* strain according to claim 1 to said human or pet food product or cosmetic composition.

10. The method according to claim 8, wherein the human or pet food product or the cosmetic composition comprises the levan in an amount of about 0.01 to 25%.

11. The method according to claim 8, wherein the levan is is present in an amount sufficient to provide an in situ source of prebiotic fructans.

12. The method according to claim 8, wherein the levan is an immunologically-stimulating polysaccharide.

13. The method according to claim 9, in which the amount of the *Lactobacillus sanfranciscensis* strain is at least $1\times10^5$ cfu/g.

14. A human or pet food product comprising the levan according to claim 3.

15. A dry infant formula comprising: 5 to 20% of peptides, 2 to 40% of fat, 10 to 60% of non-levan carbohydrates, 1 to 10% of levan according to claim 3, and, optionally, traces of vitamins and oligoelements, and 0.1 to 5% of minerals.

16. An infant formula comprising 0.5 to 5% of peptides, 0.2 to 10% of fat, 1 to 25% of non-levan carbohydrates, 0.5 to 20% of levan according to claim 3, 50% to 90% water, and, optionally, traces of vitamins and oligoelements, and 0.01 to 2% of minerals.

17. A fermented food product comprising the levan according to claim 3.

18. A human or pet food product comprising the *Lactobacillus sanfranciscensis* strain according to claim 1.

19. The human or pet food product according to claim 18, which comprises the levan in the amount of about 0.01 to 25%.

20. The human or pet food product according to claim 18, in which the amount of the *Lactobacillus sanfranciscensis* strain is at least $1\times10^5$ cfu/g.

* * * * *

UNITED STATES PATENT AND TRADEMARK OFFICE
CERTIFICATE OF CORRECTION

PATENT NO.    : 6,932,991 B2
DATED         : August 23, 2005
INVENTOR(S)   : Sebastien Vincent et al.

It is certified that error appears in the above-identified patent and that said Letters Patent is hereby corrected as shown below:

Title page,
Item [54], Inventors, change "Pully (CH)" to -- Lutry (CH) --.
Item [56], References Cited, OTHER PUBLICATIONS, "Geel-Schutten et al." reference, first occurrence, change "Geel-Schutten" to -- van Geel-Schutten --.
"Geel-Schutten et al." reference, second occurrence, change "Geel-Schutten" to -- van Geel-Schutten --; and after "Applied Microbiology and Biotechnology," delete "vol. 65, No. 11, pp. 5003-5008 (1999)" and insert -- Vol. 50, No. 6, pp. 697-703 (1998) --.
"J. Hugenholtz" reference, change "matabolism" to -- metabolism --; and change "productin" to -- producing --.
"P.J. Looijesteijn" reference, after "*Lactococcus lactis*" insert -- subsp. *cremoris* by the sugar source --.
"F. Stingle" reference, change "Stingle" to -- Stingele --; change "lh59" to -- Lh59 --; and change "and exopolysaccharide theis is identical to theone produced" to -- an exopolysaccharide that is identical to the one produced --.
"M. Staaf" reference, delete "vol. 302 No. 3-4, pp. 197-202 (1997)" and insert -- Vol. 291, pp. 155-164 (1996) --.

Column 12,
Line 17, delete the second occurrence of "is".

Signed and Sealed this

Twenty-second Day of November, 2005

JON W. DUDAS
*Director of the United States Patent and Trademark Office*